United States Patent
Fang et al.

(10) Patent No.: US 10,087,219 B2
(45) Date of Patent: Oct. 2, 2018

(54) HUMAN ALPHA-DEFENSIN 5 VARIANT AND USES THEREOF

(71) Applicant: Zhejiang University, Hangzhou, Zhejiang Province (CN)

(72) Inventors: Xiangming Fang, Hangzhou (CN); Ruyi Lei, Hangzhou (CN); Qixing Chen, Hangzhou (CN); Jinchao Hou, Hangzhou (CN); Baoli Cheng, Hangzhou (CN); Yue Jin, Hangzhou (CN)

(73) Assignee: Zhejiang University, Hangzhou, Zhejiang Province (CN)

( * ) Notice: Subject to any disclaimer, the term of this patent is extended or adjusted under 35 U.S.C. 154(b) by 0 days.

(21) Appl. No.: 15/459,467

(22) Filed: Mar. 15, 2017

(65) Prior Publication Data

US 2018/0016308 A1    Jan. 18, 2018

(30) Foreign Application Priority Data

Jul. 14, 2016    (CN) .......................... 2016 1 0561665

(51) Int. Cl.
*C07K 14/00* (2006.01)
*C07K 14/435* (2006.01)
*A61K 38/00* (2006.01)
*A61K 38/16* (2006.01)

(52) U.S. Cl.
CPC ............ *C07K 14/435* (2013.01); *A61K 38/00* (2013.01)

(58) Field of Classification Search
CPC ........ A61K 38/00; A61K 38/16; C07K 14/00; C07K 14/435; C07K 14/4723
USPC ........................... 530/300, 324; 514/1.1, 21.3
See application file for complete search history.

(56) References Cited

U.S. PATENT DOCUMENTS 5,641,497 A * 6/1997 Bevins ............... C07K 14/4723
424/405

OTHER PUBLICATIONS

Nelson et al, "Myrisoyl-Based Transport of Peptides into Living Cells," Biochemistry, 2007, 46(51): 14771-14781.*
State Intellectual Property Office of the People's Republic of China, Notice of First Office Action, dated Jan. 20, 2017.
Agnieszka Szyk et al., Crystal Structures of human a-defensins HNP4, HD5, and HD6, Protein Science, Dec. 21, 2006, pp. 2749-2760, vol. 12, No. 15.
Yue Wang et al., Advances in Research on Modification of Protein and Peptide Drugs with Fatty Acids, Progress in Pharmaceutical Sciences, Sep. 25, 2015, pp. 651-658, vol. 39, No. 9.

* cited by examiner

*Primary Examiner* — Julie Ha
(74) *Attorney, Agent, or Firm* — Shuang Chang; PSK IntellectualProperty Group, LLC

(57) ABSTRACT

A human α-defensin 5 variant is obtained by adding amino acid residues at C-terminal of α-defensin 5 and then being modified to link an aliphatic acid. At least one of the added amino acid residues has a free amino group, and the free amino group is modified to link an aliphatic acid with 8-24 carbon atoms. The variant is used in manufacture of an antibacterial agent and an immunomodulatory agent. Antibacterial activity is significantly enhanced by extending and modifying the C-terminal of HD-5; in particular, salt tolerance is significantly improved by extending the C-terminal of HD-5 with Lys and then being modified with myristic acid, thereby breaking the restriction of salt-sensibility of conventional antimicrobial peptides. The variant can significantly promote release of inflammatory factors from macrophages and thus can be applied in manufacture of immunomodulatory agent.

4 Claims, 3 Drawing Sheets

Specification includes a Sequence Listing.

HUMAN ALPHA-DEFENSIN 5 VARIANT AND USES THEREOF

CROSS-REFERENCE TO RELATED APPLICATION

This non-provisional application claims priority to and benefit of, under 35 U.S.C. § 119(a), Patent Application No. 201610561665.9 filed in P.R. China on Jul. 14, 2016, the entire content of which is hereby incorporated by reference.

FIELD OF THE INVENTION

The present invention relates to the field of biotechnology, particularly relates to a human alpha ($\alpha$)-defensin 5 variant and uses thereof.

BACKGROUND OF THE INVENTION

Antibiotic resistance is a major scientific issue threating human health. Broad spectrum even extended-spectrum drug-resistant bacteria such as methicillin-resistant *Staphylococcus aureus* (MRSA), pan-resistant *Acinetobacter baumannii*, carbapenems-resistant *Pseudomonas aeruginosa* render treatment of some infections difficult, and act as important dangerous factors in death of patients with these infections. At present, the mutational speed of drug-resistant bacteria is faster than the development of novel antibacterial drugs, and people are helpless to treat some drug-resistant bacteria and challenged with so-called "post-antibiotic era". Hence, it is extremely urgent to develop novel antibacterial drugs, especially new drugs having bactericidal ability to broad and extended spectrum drug-resistant bacteria.

Cationic antibacterial peptides are a group of small molecular polypeptides with broad spectrum antibacterial activity, and act as important immune defense for organisms to combat microorganism invasion. Cationic antibacterial peptides have antibacterial effects featured with fast bactericidal speed, broad bactericidal spectrum and difficult to develop resistance, and thus have been regarded as ideal candidates for novel antibiotics. The action mechanism of cationic antibacterial peptides relates to positive charges carried thereon, which can bind to bacterial surface with negative charges, embed in bacterial cell membrane, form voids and destroy membranal integrity, so that bacterial cytoplasm drains and bacteria die finally. In comparison with bactericidal targets of conventional antibiotics such as protein bodies, RNA enzymes, the cationic antibacterial peptides have direct, rapid and strong bactericidal potency, and are not prone to inducing conventional drug-resistances relying on gene mutation, hydrolases and so on. Some antibacterial peptides have been used as antibiotics against drug-resistant bacteria, and entered clinical trial (M. Zasloff, Nature, 2002, 415, 389-395).

Human defensin-5 (HD-5) is a natural cationic antibacterial peptide mainly expressed on intestinal mucosa, and has relatively strong bactericidal effects on many bacteria such as *Escherichia coli, Staphylococcus aureus, Bacillus cereus, Enterobacter aerogenes* and *fugi*. In addition, HD-5 exerts immunomodulatory effects via regulating release of intestinal local inflammatory factors. Hence, HD-5 plays a very important role in intestinal immuno-barrier.

Although the extraction and artificial synthesis of HD-5 are conventional now, when completely simulating natural HD-5, the antibacterial activity is prone to being influenced by many in vivo environmental factors, for example, the presence of sodium chloride in physiological concentration may extremely deduce the antibacterial activity, which restrict the use of HD-5 in developing novel antibacterial drugs suitable for industrial production and clinical application.

Hence, the present invention intends to modify HD-5 according to physical and chemical properties of HD-5, overcome functional drawbacks of HD-5 and make it to be promising in developing novel antibacterial drugs.

SUMMARY OF THE INVENTION

The present invention provides a human $\alpha$-defensin 5 variant, in which the C-terminal of human $\alpha$-defensin 5 links to aliphatic acid chains with different lengths so as to convert it into a cationic amphipathic self-assembly nano-antibacterial peptide, and obtain an artificial antibacterial peptide with good stability, high performance, being suitable for industrial production and having multiple functions.

The human $\alpha$-defensin 5 variant is obtained by adding amino acid residues at C-terminal of $\alpha$-defensin 5 and then being modified to link an aliphatic acid, wherein at least one of the added amino acid residues has a free amino group, and the free amino group is modified to link an aliphatic acid with 8-24 carbon atoms.

In the present invention, the modification uses HD-5 as template. The HD-5 consists of 32 amino acid residues, in which there are 6 cysteines pairwise forming disulfide bonds between the 1st and the 6th, the 2nd and the 4th, the 3rd and the 5th cysteines from N-terminal to C-terminal, that is, there are 3 disulfide bonds in total. In the present invention, the C-terminal is extended to finally obtain the variant of the present invention.

Our researches indicate that the modification of C-terminal of HD-5 with aliphatic acid could significantly enhance bactericidal activity of human $\alpha$-defensin 5, and the variant obtained by C-terminal modification has stronger bactericidal potency than variant obtained by N-terminal modification.

The variant of the present invention has features of potent bactericidal activity and low hemolysis rate. Preferably, the aliphatic acid has carbon atoms in number of 12-14. More preferably, the aliphatic acid is myristic acid or lauric acid.

In the present invention, adding amino acids at C-terminal to extend peptide chain facilitates modification of aliphatic acid. Preferably, the added amino acid residues are in a number of 2-5.

The modification with aliphatic acid is carried out via condensation reaction between carboxyl of aliphatic acid and free amino group of C-terminal amino acid residue. Hence, the amino acids added at C-terminal of HD-5 variant include at least one amino acid having at least two amino groups, for example, Lys, in which the $\alpha$ amino group is used for synthesizing peptide bond of peptide chain, while the amino group at side chain is used for modification of aliphatic acid chain.

Preferably, the variant has a peptide chain consisting of 34 amino acid residues which amino acid sequence is as follows:

Ala1-Thr2-Cys3-Tyr4-Cys5-Arg6-Thr7-Gly8-Arg9-Cys10-Ala11-Thr12-Arg13-Glu14-Ser15-Leu16-Ser17-Gly18-Val19-Cys20-Glu21-Ile22-Ser23-Gly24-Arg25-Leu26-Tyr27-Arg28-Leu29-Cys30-Cys31-Arg32-Gly33-Lys34 (SEQ ID NO: 2).

Preferably, the C-terminal of the variant is amidated.

In the present invention, the C-terminal amidation is performed at the 34th Lys of the sequence, and the $\epsilon$ amino group is linked to myristoyl or lauroyl, which are named as HD-5Myr and HD-5Lau, respectively. Our researches indicate that the variants HD-5Myr and HD-5Lau have bactericidal effects on both gram-positive bacteria and gram-negative bacteria. HD-5Myr and HD-5Lau can form micellar structure. The formation of micellar structure makes these peptides aggregate from monomer to multimer form in nano-scale, and makes positive charges be more concentrated, so that its binding ability to bacteria is stronger and it can exhibit more potent bactericidal effects.

The present invention further provides a use of the human α-defensin 5 variant in manufacture of an antibacterial agent.

With regard to *Staphylococcus aureus* ATCC 25923, the $LD_{90}$ value of HD-5Myr is about ¼ of that of HD-5, while the $LD_{90}$ value of HD-5Lau is about ⅓ of that of HD-5; with regard to *Escherichia coli* ATCC 25922, the $LD_{90}$ value of HD-5Myr is less than ⅛ of that of HD-5, while the $LD_{90}$ value of HD-5Lau is less than ⅙ of that of HD-5, which indicates HD-5Myr and HD-5Lau have bactericidal activity stronger than HD-5. With regard to methicillin-resistant *Staphylococcus aureus* MRSA-1 isolated in clinic, the $LD_{90}$ value of HD-5Myr is about 1/15 of that of HD-5, while the $LD_{90}$ value of HD-5Lau is about ¼ of that of HD-5.

The $LD_{90}$ values of HD-5, HD-5Myr and HD-5Lau against methicillin-resistant *Staphylococcus aureus* are far lower than corresponding $LD_{90}$ values against *Staphylococcus aureus* ATCC 25923, which indicates their antibacterial mechanism is different from those of conventional antibiotics. Hence, the variants HD-5Myr and HD-5Lau of the present invention can be used in manufacture of medicaments for combating drug-resistant bacteria.

With respect to salt-resistance, HD-5Myr is significantly stronger than HD-5Lau and HD-5, and can exert potent bactericidal effects even under physiological concentration (sodium chloride concentration is 135 mM to 145 mM). Hence, HD-5Myr can be used as a potent antibacterial component in manufacture of an intravenous injection.

The present invention further provides a use of the human α-defensin 5 variant in manufacture of an immunomodulatory agent.

Our researches indicate that the variants HD-5Myr and HD-5Lau can promote release of inflammatory factors IL-1β from macrophages. IL-1β plays an important role in immunomodulatory procedure. Hence, the variants HD-5Myr and HD-5Lau can be used in manufacture of an immunomodulatory agent.

The present invention further provides a pharmaceutical composition, characterized in comprising the human α-defensin 5 variant and a pharmaceutically acceptable carrier.

When the blood concentration of the DH-5 variants reaches 25 μg/ml, high performance of bactericidal effects and lower hemolysis rate could be observed, so that they are ideal antibacterial drugs for replacement of convention antibiotics.

The beneficial effects of the present invention are as follows:

(1) In the present invention, human α-defensin 5 is extended and modified at C-terminal, so that its antibacterial activity, especially antibacterial activity against methicillin-resistant *Staphylococcus aureus*, is effectively enhanced, so that it is a promising antibacterial drug for replacement of conventional antibiotics.

(2) In the present invention, the variants HD-5Myr and HD-5Lau can form micellar structure. The formation of micellar structure makes positive charges more concentrated, so that its binding ability to bacteria is stronger and it can exhibit more potent bactericidal effects.

(3) In the present invention, human α-defensin 5 is added at C-terminal with Gly and Lys and modified with myristic acid, which significantly improve the salt-resistance of variants.

(4) In the present invention, the variants can significantly promote release of inflammatory factors from macrophages, so that they can be used in manufacture of an immunomodulatory agent.

DETAILED DESCRIPTION OF THE INVENTION

Figure 1:
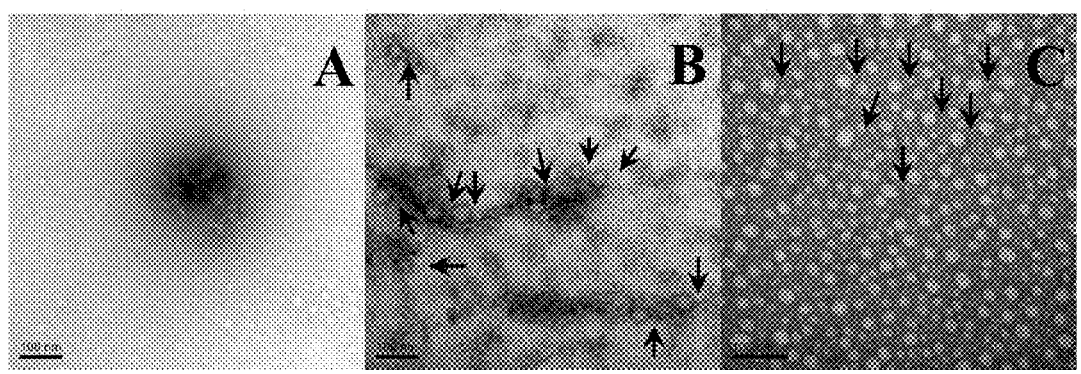
FIG. 1 shows transmission electron microscope diagrams of variants HD-5Myr and HD-5Lau of the present invention, in which A is HD-5, B is HD-5Myr, C is HD-5Lau.

In order to better understand the present invention, the present invention is further illustrated in conjugation with the following examples and figures, but the following examples are not to limit the protection scope of the present invention, and any changes and modifications based on the present invention fall within the protection scope of the present invention.

Embodiment 1

The amino acid sequence of HD-5 is shown in SEQ ID NO: 1, as follows:
Ala1-Thr2-Cys3-Tyr4-Cys5-Arg6-Thr7-Gly8-Arg9-Cys10-Ala11-Thr12-Arg13-Glu14-Ser15-Leu16-Ser17-Gly18-Val19-Cys20-Glu21-Ile22-Ser23-Gly24-Arg25-Leu26-Tyr27-Arg28-Leu29-Cys30-Cys31-Arg32 (SEQ ID NO: 1), in which, intramolecular disulfide bonds are formed between Cys3 and Cys31, Cys5 and Cys20, Cys10 and Cys30, respectively.

In the present invention, the variants HD-5Myr and HD-5Lau were obtained on basis of HD-5 molecule via modification of its C-terminal. The amino acid sequences of HD-5Myr and HD-5Lau are shown in SEQ ID NO: 2.

HD-5Myr consisted of 34 amino acid residues, having a molecular weight of 3976.8 Da.

HD-5Myr has an amino acid sequence as follows:
Ala1-Thr2-Cys3-Tyr4-Cys5-Arg6-Thr7-Gly8-Arg9-Cys10-Ala11-Thr12-Arg13-Glu14-Ser15-Leu16-Ser17-Gly18-Val19-Cys20-Glu21-Ile22-Ser23-Gly24-Arg25-Leu26-Tyr27-Arg28-Leu29-Cys30-Cys31-Arg32-Gly33-Lys34-NH2 (SEQ ID NO: 2), in which, intramolecular disulfide bonds are formed between Cys3 and Cys31, Cys5 and Cys20, Cys10 and Cys30. The 34th position is Lys, the ε amino group is linked to a myristoyl.

HD-5Lau consisted of 34 amino acids, having a molecular weight of 3948.7 Da.

HD-5Lau has an amino acid sequence as follows:
Ala1-Thr2-Cys3-Tyr4-Cys5-Arg6-Thr7-Gly8-Arg9-Cys10-Ala11-Thr12-Arg13-Glu14-Ser15-Leu16-Ser17-Gly18-Val19-Cys20-Glu21-Ile22-Ser23-Gly24-Arg25-

Leu26-Tyr27-Arg28-Leu29-Cys30-Cys31-Arg32-Gly33-Lys34-NH2 (SEQ ID NO: 2), in which, intramolecular disulfide bonds are formed between Cys3 and Cys31, Cys5 and Cys20, Cys10 and Cys30. The 34th position is Lys, the ε amino group is linked to a lauroyl.

In addition, based on HD-5, its N-terminal was modified to obtain a variant, which was named as MyrHD-5. MyrHD-5 consists of 33 amino acid residues, having a molecular weight of 3849.6 Da.

MyrHD-5 has an amino acid sequence of as shown in SEQ ID NO: 3, as follows:

Gly1-Ala2-Thr3-Cys4-Tyr5-Cys6-Arg7-Thr8-Gly9-Arg10-Cys11-Ala12-Thr13-Arg14-Glu15-Ser16-Leu17-Ser18-Gly19-Val20-Cys21-Glu22-Ile23-Ser24-Gly25-Arg26-Leu27-Tyr28-Arg29-Leu30-Cys31-Cys32-Arg33 (SEQ ID NO: 3), in which, intramolecular disulfide bonds are formed between Cys4 and Cys32, Cys6 and Cys21, Cys11 and Cys31. The 1st position is Gly, the amino group is linked to a myristoyl.

Embodiment 2

HD-5 and HD-5Myr in Example 1 were synthesized by "Shanghai Gill Polypeptide Co., Ltd.". HD-5Lau and MyrHD-5 in Example 1 were synthesized by "Hangzhou China Peptide Biochemical Co., Ltd.".

Embodiment 3

According to measurement of antibacterial activity of antibacterial peptides, the antibacterial potencies of the variants HD-5Myr, HD-Lau and MyrHD-5 of HD-5 as synthesized in Example 2 as well as natural HD-5 were compared.

The experiments were carried out according to the method for detecting antibacterial activity of antibacterial peptide as reported by Ericksen et al in 2005 (Ericksen B, et al., Antibacterial activity and specificity of the six human {alpha}-defensins. Antimicrob Agents Chemother, 2005).

Bacteria were inoculated on LB agar plate, and placed in 37° C. constant temperature incubator until bacterial colonies grew. Single colony was picked out, inoculated in 5 ml of LB culture media, and shake cultured at constant temperature of 37° C. for 4-6 h. It was then washed with sterile water twice. Optical density at 600 nm was measured with ELIASA, 1 OD600=4×10$^8$ CFU/ml, and the bacteria to be tested were diluted with sterile water to 2×10$^6$ CFU/ml.

To a sterile 96-plate, 50 μl of sterile water was added to each well, and then A1 well was added with an antibacterial peptide HD-5 sample diluted to a certain concentration. After being mixed evenly, 50 μl was taken therefrom and added to A2 well, thereby being diluted in multiple proportion manner in order, and 50 μl was sucked out from A6 well and discarded. By using the same method, MyrHD-5, HD-5Myr and HD-5Lau samples were diluted. The control well was 50 μl sterile water. Then, to each well, 50 μl of 2×10$^6$ CFU/ml bacteria was added, and shake cultured at constant temperature of 37° C. for 2 h. Then, 100 μl of LB culture media with double concentration was added separately. Optical density values at 600 nm were measured every 5 minutes in ELIASA at constant temperature of 37° C.

The measured optical density value minus the optical density value at time 0, and logarithm thereof was taken. In a coordinate system, by using time as abscissa and using logarithm of change value of OD value as ordinate, the obtained points were in linear during logarithmic phase. According to this linear rule, bactericidal rates for different groups were calculated. According to the bactericidal rates at different concentrations, the concentration of antibacterial peptide required for killing 90% bacteria was calculated, and called as $LD_{90}$. The $LD_{90}$ values of HD-5 as well as MyrHD-5, HD-5Myr and HD-5Lau to different bacteria were shown in Table 1.

TABLE 1

Antibacterial activities of antibacterial peptide HD-5 and its variants

| Bacteria tested | HD-5, $LD_{90}$ (μg/ml) | HD-5Myr, $LD_{90}$ (μg/ml) | HD-5Lau, $LD_{90}$ (μg/ml) | MyrHD-5, $LD_{90}$ (μg/ml) |
|---|---|---|---|---|
| E. coli ATCC 25922 | 6.691 | 1.601 | 2.027 | >12.5 |
| S. aureus ATCC 25923 | >12.5 | 1.602 | 2.187 | 6.280 |
| MRSA-1 | 5.850 | 0.383 | 1.557 | 1.400 |

The E. coli ATCC 25922, S. aureus ATCC 25923 were purchased from American Type Culture Collection (ATCC). MRSA-1 was methicillin-resistant Staphylococcus aureus isolated in clinic.

It can be seen in Table 1 that HD-5Myr and HD-5Lau have killing effects on gram-positive Staphylococcus aureus, gram-negative Escherichia coli and MRSA-1 as isolated in clinic, and the variants HD-5Myr and HD-5Lau have effects superior to wild peptide HD-5.

The above experimental results show that the HD-5Myr and HD-5Lau in the experiment show antibacterial activities superior to natural HD-5, either against gram-positive Staphylococcus aureus, or gram-negative Escherichia coli, or methicillin-resistant Staphylococcus aureus isolated in clinic; and HD-5Myr and HD-5Lau have antibacterial potencies to MRSA superior to those to methicillin-sensitive Staphylococcus aureus ATCC 25923, which indicate that their antibacterial mechanism is different from those of conventional antibiotics.

Both MyrHD-5 and HD-5Myr are variants obtained by modifying HD-5 molecule with myristoyl, in which MyrHD-5 is modified at N-terminal, while HD-5Myr is modified at C-terminal; however, HD-5Myr has bactericidal potency significantly superior to MyrHD-5. In addition, MyrHD-5 exhibits potency of killing E. coli ATCC 25922 stains even inferior to HD-5. This indicated that aliphatic acid modification at C-terminal of HD-5 molecule is more beneficial to exerting bactericidal effects.

Embodiment 4

The variants HD-5Myr and HD-5Lau of antibacterial peptide could form micellar structure, which further facilitates their bactericidal effects.

Small amounts of HD-5, HD-5Myr and HD-5Lau samples were taken and dropped on copper grid used for electron microscope, excessive samples were sucked out with filter paper, after being dried at room temperature, uranyl acetate was used for staining. Then the samples were observed with a transmission electron microscopy.

As shown in FIG. 1A, micellar structure was not observed in natural HD-5. As indicated with arrow in FIG. 1B, HD-5Myr could form micellar structure. As indicated with arrow in FIG. 1C, globular granules with uniform size were micellar structure, which indicated that HD-5Lau could form micellar structure. The formation of micellar structure made these peptides aggregate from monomer to multimer in nano-scale, and made positive charges be more concentrated, so that its binding ability to bacteria with negative charges was stronger, which facilitated its penetration through cell wall and cell membrane of bacteria, thereby exhibiting more potent bactericidal effects.

Embodiment 5

Salt-tolerances of antibacterial peptide HD-5 as well as its variants HD-5Myr and HD-5Lau in term of antibacterial activity were studied.

The experiment was carried out according to the method for detecting antibacterial activity of antibacterial peptide as reported by Ericksen et al in 2005 (Ericksen B, et al., Antibacterial activity and specificity of the six human {alpha}-defensins. Antimicrob Agents Chemother, 2005).

Bacteria were inoculated on LB agar plate, and placed in 37° C. constant temperature incubator until bacterial colonies grew. Single colony was picked out, inoculated in 5 ml of LB culture media, and shake cultured at constant temperature of 37° C. for 4-6 h. It was then washed with sterile water twice. Optical density at 600 nm was measured with ELIASA, 1 OD600=4×10$^8$ CFU/ml, and the bacteria to be tested were diluted with sterile water to 2×10$^6$ CFU/ml.

To each of A1 to A6 wells, 25 μl of NaCl solution with certain concentration was added. Then, to each well, 25 μl of 100 μg/ml HD-5 solution was added. The same method was applied to HD-5Myr group and HD-5Lau group. The control well was a mixture solution of 25 μl of salt solution with different concentration and 25 μl of sterile water. Then, to each well 50 μl of 2×10$^6$ CFU/ml E. coli (ATCC 25922) was added, and shake cultured at constant temperature of 37° C. for 2 h. Then, 100 μl of LB culture media with double concentration was added separately. Optical density values at 600 nm were measured every 5 minutes in ELIASA at constant temperature of 37° C.

The measured optical density value minus the optical density value at time 0. By using time as abscissa and using change value of OD value as ordinate, a curve was plotted. According to the length of time period to reach a certain OD value in the curve, the survival amount of bacteria at time 0 was deduced, and then the effects of salt on its bactericidal effects were evaluated.

Figure 2:
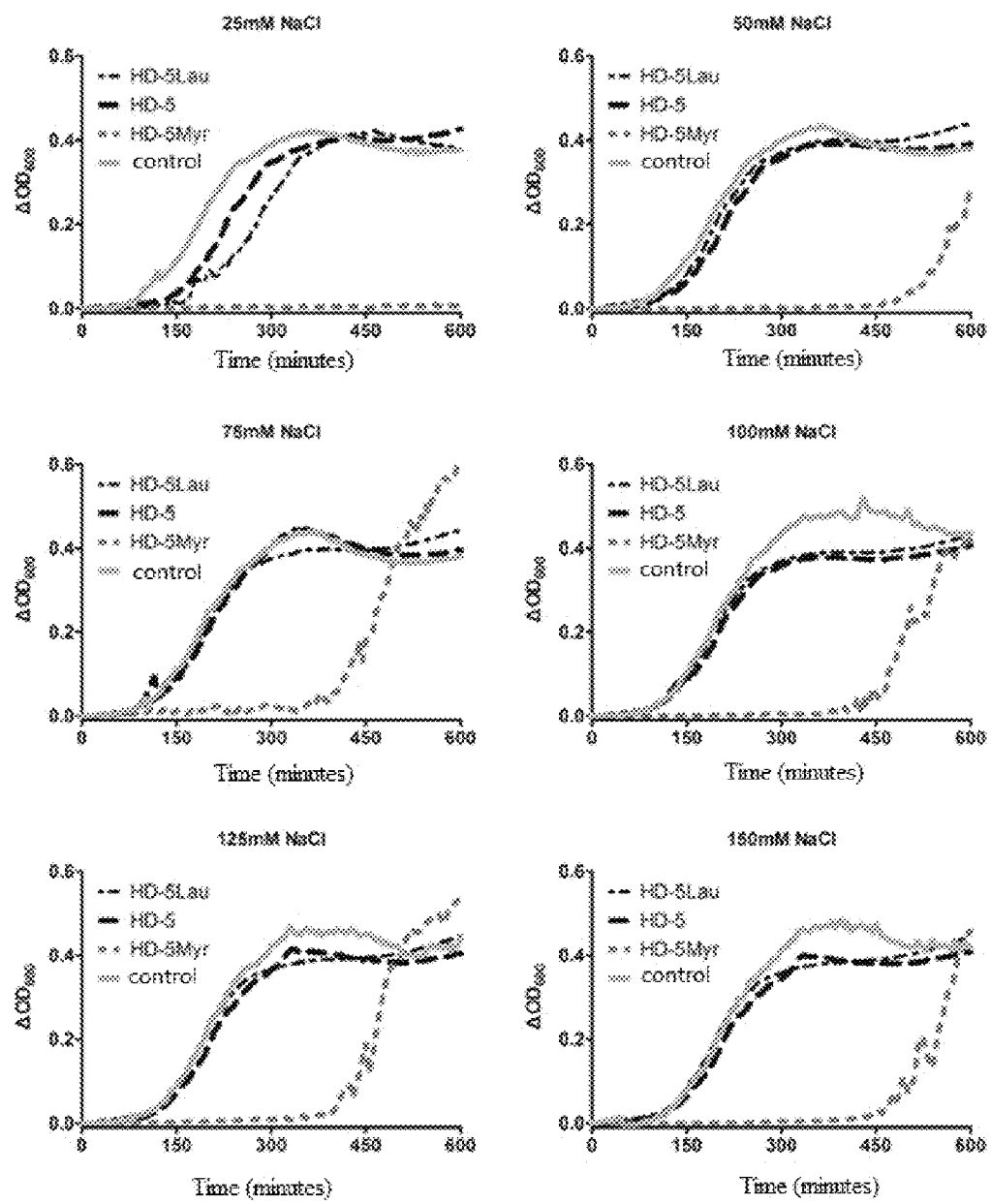
FIG. 2 shows diagrams of antibacterial activity results of HD-5 and variants, as described in Example 5 under conditions of different sodium chloride concentrations.

As shown in FIG. 2, the salt-tolerance of HD-5Myr was significantly superior to HD-5 and HD-5Lau. Even under condition of sodium chloride solution with physiological concentration (135 mM-145 mM), HD-5Myr could still exert potent bactericidal effects.

Embodiment 6

The hemolysis effects of antibacterial peptide HD-5 as well as its variants HD-5Myr and HD-5Lau on human red cell were measured.

Fresh human blood sample was collected, heparinized then centrifuged to take red cell layer;
washed with PBS for 3 times;
to EP tube, HD-5 and its variants with final concentrations of 50 μg/ml and 25 μg/ml were added separately; the positive control was added with 10% Triton X-100 in same volume, while the negative control was added with PBS in same volume.
4% human red cells were added separately, incubated at 37° C. for 1 h;
centrifuged, supernatant in same volume was taken and placed in 96-well plate, OD value at 540 nm was measured; by using the positive control as 100% hemolysis, and using the negative control as 0% hemolysis, the hemolysis rate for each well was calculated:

Red cell hemolysis rate %=Test well OD value−negative control well OD valuePositive control well OD value−negative control OD×100%

Figure 3:
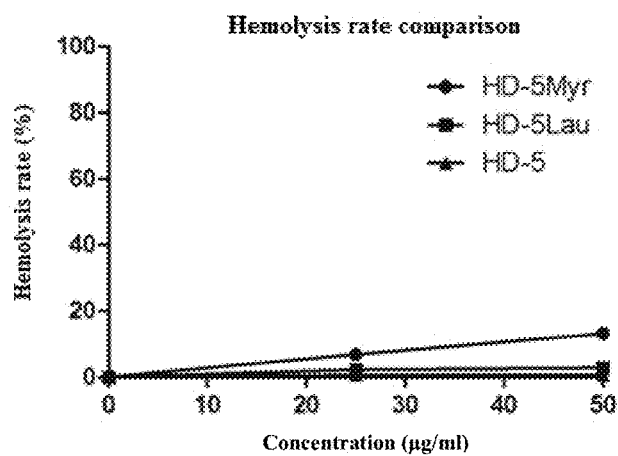
FIG. 3 shows diagrams of human red cell hemolysis results of HD-5 and variants, as described in Example 6.

As shown in FIG. 3, when LD$_{90}$ was far higher than 25 μg/ml, HD-5Myr had a hemolysis rate of 6.83%, and HD-5Lau had a hemolysis rate of 2.24%. This indicated that the variants HD-5Myr and HD-5Lau all had relatively broad safety range, which extremely facilitated their applications in field of medicals.

Embodiment 7

The variants of antibacterial peptide had immunomodulatory effects, and promoted release of inflammatory factor IL-1β.

THP-1 cells were cultured with RPMI-1640 culture media added with 10% fetal calf serum, and then inoculated on 24-well plate during logarithmic phase, 10$^6$ cells per well, added with PMA with final concentration of 100 nM for stimulating for 12 h so that cell adhered wall.

Media was exchanged with RPMI-1604 added with 10% fetal calf serum, and stood for 24 hours.

The following groups were set: blank group, LPS stimulation group, LPS+5 mM ATP group (positive control group), LPS+HD-5 group, LPS+HD-5Myr group, LPS+HD-5Lau group. 100 ng/ml lipopolysaccharide (LPS) was used or not to perform stimulation for 3 h, then gently washed twice with 1640 culture media, and then added or not with HD-5Myr or HD-5Lau with final concentration of 10 μg/ml and 20 μg/ml, or ATP with final concentration of 5 mM, or HD-5 with final concentration of 100 μg/ml and 200 μg/ml; and supernatant of each group was collected.

The proteins in supernatant in same volume were concentrated, lysed with protein lysis solution, and then release conditions of IL-1β mature body for different groups were compared by immunoblotting method.

Figure 4:
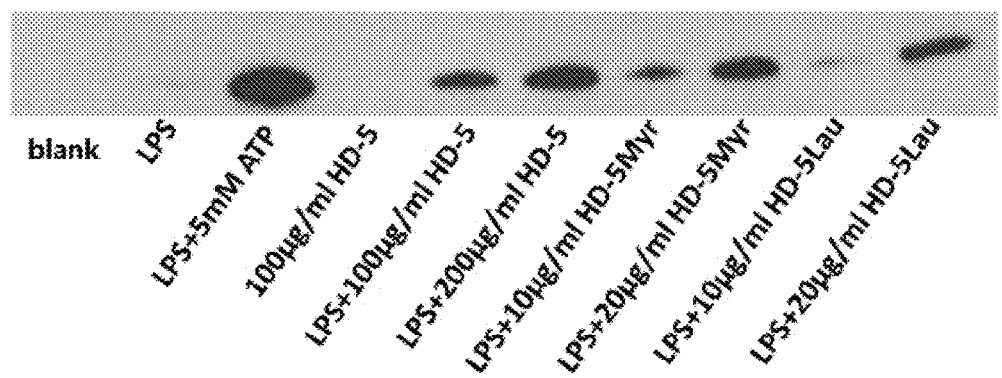
FIG. 4 shows diagrams of macrophage IL-1β mature body release results regulated by HD-5 and variants, as described in Example 7.

As shown in FIG. 4, LPS+5 mM ATP group (positive control), LPS+HD-5 group, LPS+HD-5Myr group, LPS+HD-5Lau group all exhibited release of IL-1β mature body, which confirmed that HD-5, HD-5Myr and HD-5Lau could promote the release of IL-1β mature body, while HD-5Myr and HD-5Lau were of concentrations far lower than that of HD-5, which indicated that the variants HD-5Myr and HD-5Lau had immunomodulatory activity far superior to HD-5.

What is claimed is:

1. A human α-defensin 5 variant, having a peptide chain consisting of 34 amino acid residues as follows:
$Ala^1$-$Thr^2$-$Cys^3$-$Tyr^4$-$Cys^5$-$Arg^6$-$Thr^7$-$Gly^8$-$Arg^9$-$Cys^{10}$-$Ala^{11}$-$Thr^{12}$-$Arg^{13}$-$Glu^{14}$-$Ser^{15}$-$Leu^{16}$-$Ser^{17}$-$Gly^{18}$-$Val^{19}$-$Cys^{20}$-$Glu^{21}$-$Ile^{22}$-$Ser^{23}$-$Gly^{24}$-$Arg^{25}$-$Leu^{26}$-$Tyr^{27}$-$Arg^{28}$-$Leu^{29}$-$Cys^{30}$-$Cys^{31}$-$Arg^{32}$-$Gly^{33}$-$Lys^{34}$ (SEQ ID NO: 2),
wherein the C-terminal of the variant is amidated, and the free amino group of $Lys^{34}$ is linked with myristic acid.

2. An antibacterial agent, comprising the human α-defensin 5 variant according to claim 1.

3. An immunomodulatory agent, comprising the human α-defensin 5 variant according to claim 1.

4. A pharmaceutical composition, comprising the human α-defensin 5 variant according to claim 1 and a pharmaceutically acceptable carrier.

* * * * *

SEQUENCE LISTING

<160> NUMBER OF SEQ ID NOS: 3

<210> SEQ ID NO 1
<211> LENGTH: 32
<212> TYPE: PRT
<213> ORGANISM: Homo sapiens

```
<400> SEQUENCE: 1

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

<210> SEQ ID NO 2
<211> LENGTH: 34
<212> TYPE: PRT
<213> ORGANISM: Artificial Sequence
<220> FEATURE:
<223> OTHER INFORMATION: HD-5 variant

<400> SEQUENCE: 2

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

Gly Lys

<210> SEQ ID NO 3
<211> LENGTH: 33
<212> TYPE: PRT
<213> ORGANISM: Artificial Sequence
<220> FEATURE:
<223> OTHER INFORMATION: HD-5 variant

<400> SEQUENCE: 3

Gly Ala Thr Cys Tyr Cys Arg Thr Gly Arg Cys Ala Thr Arg Glu Ser
1               5                   10                  15

Leu Ser Gly Val Cys Glu Ile Ser Gly Arg Leu Tyr Arg Leu Cys Cys
            20                  25                  30

Arg
```